United States Patent [19]

Schroeder et al.

[11] Patent Number: 4,620,029
[45] Date of Patent: Oct. 28, 1986

[54] METHOD FOR MAKING OXALIC ACID DIESTERS

[75] Inventors: Günter Schroeder, Ober-Ramstadt; Ehrenfried Baumgartner, Darmstadt, both of Fed. Rep. of Germany

[73] Assignee: Röhm GmbH, Darmstadt, Fed. Rep. of Germany

[21] Appl. No.: 668,193

[22] Filed: Nov. 5, 1984

[30] Foreign Application Priority Data

Nov. 23, 1983 [DE] Fed. Rep. of Germany ....... 3342291

[51] Int. Cl.$^4$ .............................................. C07C 67/36
[52] U.S. Cl. .................................. 560/204; 560/190; 560/193
[58] Field of Search ...................... 560/190, 204, 193

[56] References Cited

U.S. PATENT DOCUMENTS

| | | | |
|---|---|---|---|
| 3,393,136 | 7/1968 | Fenton et al. | 204/59 |
| 3,994,960 | 11/1976 | Yamazaki et al. | 560/204 |
| 4,005,128 | 1/1977 | Zehner et al. | 560/204 |
| 4,005,129 | 1/1977 | Zehner et al. | 560/204 |
| 4,076,949 | 2/1978 | Fehner | 560/204 |
| 4,118,589 | 10/1978 | Cassar | 560/204 |
| 4,138,587 | 2/1979 | Yamasaki | 562/434 |
| 4,230,881 | 10/1980 | Romano et al. | 560/193 |

FOREIGN PATENT DOCUMENTS

| | | |
|---|---|---|
| 56993 | 8/1982 | European Pat. Off. . |
| 56994 | 8/1982 | European Pat. Off. . |
| 57629 | 8/1982 | European Pat. Off. . |
| 57630 | 8/1983 | European Pat. Off. . |
| 2213435 | 10/1973 | Fed. Rep. of Germany . |
| 2514685 | 10/1975 | Fed. Rep. of Germany . |
| 2601139 | 7/1976 | Fed. Rep. of Germany . |
| 2721734 | 12/1977 | Fed. Rep. of Germany . |
| 2733730 | 2/1978 | Fed. Rep. of Germany . |
| 2814708 | 10/1978 | Fed. Rep. of Germany . |
| 1451764 | 10/1976 | United Kingdom . |

OTHER PUBLICATIONS

Kirk-Othmer, Encyclopedia of Chemical Technology, vol. 7, Interscience, p. 725, (1967).

*Primary Examiner*—Natalie Trousof
*Assistant Examiner*—Vera C. Clarke

[57] ABSTRACT

A method for making a diester of oxalic acid which comprises oxidatively carbonylating an alcohol having 1 to 10 carbon atoms with carbon monoxide and with oxygen at a pressure from 1 to 700 bars and at a temperature from 20° C. to 250° C. in a reaction phase comprising said alcohol having dissolved therein a catalyst system consisting essentially of, as cations, ions of palladium(II) and copper ions in a molar ratio of at least 0.2 and, as anions, halide ions and carboxylate ions having 1 to 6 carbon atoms, the amounts of all ions in said catalyst system being such that the solution of the cations and anions in the alcohol has a formal pH value, as determined electrometrically, between 8 and 5.

10 Claims, No Drawings

METHOD FOR MAKING OXALIC ACID DIESTERS

The present invention relates to a method for making oxalic acid diesters, particularly dimethyl oxalate, by the oxidative carbonylation of the corresponding alcohols with palladium-copper catalysts.

U.S. Pat. No. 3,393,136 teaches a process for the preparation of saturated oxalic esters wherein a substantially anhydrous reaction medium consisting of a saturated simple $C_1$–$C_{12}$ alcohol and from 0.001 to 2 percent by weight of a metal from the platinum group as well as from 0.05 to 5 percent by weight of a redox salt from the group of soluble copper(II) and iron(III) salts is contacted with carbon monoxide, and concurrently with oxygen to maintain the redox salt in its highest oxidation state, at temperatures ranging from 30° C. to 300° C. and pressures ranging from 5 to 700 bars.

Published German patent application No. DOS 22 13 435 also proposes a method for the preparation of oxalic acid and its esters wherein carbon monoxide in an aqueous or alcoholic phase is oxidized with oxygen under pressure and at elevated temperature in the presence of a catalyst system composed of a salt or of a complex compound of a platinum metal and of a salt or complex of another metal which is more electropositive than said noble metal and which can occur in several oxidation states. Moreover the conversion of insoluble or difficulty soluble platinum-metal salts to soluble complexes by the addition of an alkali metal salt is claimed.

Published German patent application No. DOS 25 14 685 (=U.S. Pat. No. 3,994,960) teaches a process for the preparation of dialkyl oxalates by reaction of an aliphatic alcohol with carbon monoxide and oxygen under pressure in the presence of a catalyst consisting of a mixture of a salt, of a metal from the platinum group, and of a salt of copper or iron, optionally in the presence of an alkali metal salt, the reaction being carried out in the presence of an accelerator consisting of one or more compounds from the group of carbonates, bicarbonates, nitrates, sulfates, hydroxides, and carboxylates of alkali metals or alkaline earth metals, as well as pyridine, quinoline, glycine, alanine, urea, thiourea, formamide, acetamide, acetylacetone, ethyl acetoacetate, dimethylglyoxime, tertiary amines, and substituted or unsubstituted triphenyl-phosphines.

From the chemical point of view, the group of said "accelerators" is quite heterogeneous. It includes inorganic bases such as the alkali metal hydroxides and carbonates, for example, in addition to neutral substances known for their drying action, such as $Na_2SO_4$ and $MgSO_4$ The effect of nitrates is probably due to the participation, in the redox processes of the oxidative carbonylation, of nitrites or esters formed. (See also published European patent publications Nos. 56,993 and 56,994, published German patent application No. DOS 27 33 730 (=U.S. Pat. No. 4,138,587), and published European patent publications Nos. 57,629 and 57,630.)

Published German patent applications No. DOS 26 01 139 (=U.S. Pat. No. 4,118,589) teaches a process characterized by the concurrent use of ammonia or amines.

Published German patent application No. DOS 27 21 734 (=U.S. Pat. No. 4,076,949) proposes an improvement wherein a halide free ammonium salt is used, in addition to amines, and the copper(II) compound should also be free of halide ions.

While the general suitability of noble metal catalysts from the platinum group in combination with redox systems such as copper(II) or iron(III) for the catalysis of the oxidative carbonylation of alcohols is apparent from the prior art, the different variants proposed offer a rather confusing if not actually contradictory picture.

As mentioned above, published German patent application No. DOS 25 14 685 (=U.S. Pat. No. 3,994,960) attributes accelerator action not only to alkaline compounds (such as alkali metal hydroxides and amines) and neutral compounds (such as sodium sulfate, magnesium sulfate and the acid amides), but also to protic complexing agents (such as acetylacetone, acetoacetic esters, and dimethylglyoxime).

U.S. Pat. Nos. 4,005,128 and 4,005,129 disclose processes for the synthesis of oxalates from an alcohol, carbon monoxide, and oxygen in the presence of catalysts including platinum, palladium, or copper, at least stoichiometric amounts of an amine or ammonia and at least stoichiometric amounts of an "oxidant salt compounds", such as of copper (II) or iron (III), which salt compound is not a halide.

Published German patent application No. DOS 28 14 708 (=U.S. Pat. No. 4,230,881) recommends the use of acidic co-catalysts.

The results of the processes for the preparation of oxalic acid esters by oxidative carbonylation of alcohols using oxygen as the oxidant generally leave much to be desired. They only partly meet important requirements for their practice on a commercial scale, such as a high space-time yield, high selectivity, and suitability for continuous operation, as well as economic requirements such as reasonable starting up and operating costs. In the light of past experience, catalyst systems which are heterogeneous from the outset, for example, systems using alkali carbonate or bicarbonate addition, are also technically unsatisfactory.

Particularly disturbing is that a decline in the efficiency of the process is often observed with prolonged duration of the catalytic process. A causal relationship between that decline and specific chemical and/or physical properties has not been apparent up to now.

The present invention is largely based on a recognition of the fact that the reaction rate and the yield of oxalic acid diesters are dependent in large measure on the formal pH value of the reaction medium. Moreover, the solubility of the employed catalyst system in the alcoholic reaction phase appears to be an important prerequisite for a technically satisfactory production process.

It has been found that the method for making diesters of oxalic acid by the reaction of carbon monoxide with alcohols in the presence of oxygen (oxidative carbonylation) at pressures ranging from 1 to 700 bars, and preferably from 1 to 250 bars, and at temperatures ranging from 20° C. to 250° C., and preferably from 70° C. to 200° C., wherein the alcoholic reaction phase contains palladium(II) salts and copper compounds as catalysts, will produce substantially better results when (a) alcohols having from 1 to 10 carbon atoms, and particularly primary and secondary alcohols, are used;

(b) a catalyst system soluble in the alcohols according to (a) and consisting only of palladium(II) ions, copper ions, and optional alkali metals ions as cations, and halide anions and anions of a carboxylic acid having a total of from 1 to 6 carbon atoms as anions, is used;

(c) the amounts of all ions according to (b) are such that the solutions of the cations and anions in the alcohols as reaction phase present at the start of the reaction have a formal pH value, as determined electrometrically between 8 and 5; and (d) the molar ratio of palladium(II) ions to copper ions in the reaction phase according to (c) is equal to or greater than 0.2.

The formal pH value is determined electrometrically by the equation $$pH = \frac{(E_o - E)}{F_N},$$

wherein $E_o$ = standard potential of the glass electrode in an aqueous solution of pH=0,
$E$ = measured potential of the reaction medium, and
$F_N$ = Nernst factor.

(See K. Schwabe, "Elektrochemische pH-Messungen unter extremen Bedingungen", Verlag Chemie, 1960.)

For the course of the reaction underlying the present oxidative carbonylation, the following formula scheme may be established to illustrate the redox processes when copper(II) salts are used with palladium compounds:

$$2ROH + 2CO + Pd^{2+} = RO-\overset{O}{\overset{\|}{C}}-\overset{O}{\overset{\|}{C}}-OR + 2H^+ + Pd^o \quad (A)$$

$$Pd^o + 2Cu^{2+} = Pd^{2+} + 2Cu^+ \quad (B)$$

(B) $Pd^o + 2Cu^{2+} = Pd^{2+} + 2Cu^+$
(C) $2Cu^+ + 2H^+ + \frac{1}{2}O_2 = 2Cu^{2+} + H_2O$, ROH meaning, in the case of the present process, an alcohol having from 1 to 10 carbon atoms.

When the carbonylation step (A) proceeds at a faster rate than the reoxidation process (C), as is hypothesized, the pH value will shift into the acidic region.

It will be advantageous to carry out the process at a reaction temperature of at least 70° C. A preferred temperature range is 70° C. to 200° C. The pressure will usually range from 1 to 250 bars.

It has been found advantageous to choose such reaction conditions that the carbon monoxide partial pressure in bars has a greater numerical value than the reaction temperature in degrees Celsius minus 10° C.

The molar ratio of carbon monoxide to oxygen in the reaction mixture is preferably 4:1.

From the point of view of an industrial use of the ester products, alcohols having from 1 to 10 carbon atoms, and particularly primary—but also secondary and tertiary—alcohols, are preferred.

At the same time, a catalyst system soluble in the alcohol should be established in the reaction phase. In other words, the reaction phase should be a homogeneous solution.

Examples of suitable alcohols are ethanol, n-propanol, isopropanol, n-butanol, n-hexanol, cyclohexanol, and especially methanol. Suitable halide anions are fluorides, chlorides, bromides, and iodides, and preferably halides with an atomic number of at least 17, in other words, chlorides, bromides, and iodides. Illustrative of suitable catalysts are, in particular, palladium(II) chlorides and bromides. Suitable copper compounds forming the copper ions soluble in the alcohols are copper(II) salts, and particularly copper(II) halides such as the chlorides, bromides, and iodides, in addition to the copper(II) salts of carboxylic acids. Therefore, suitable copper salts are also those with anions of a carboxylic acid having a total of 1 to 6 carbon atoms. The same applies to the palladium salts, the qualitative and quantitative composition of the catalyst system being governed by observance of the requirement for an electrometically determined formal pH value between 8 and 5.

Particularly well suited are the salts of acetic acid, propionic acid, and pivalic acid. Copper(II) acetate is of special interest.

The catalyst system may further include alcohol soluble alkali metal salts.

Suitable cations are lithium, sodium, and potassium, and suitable anions are chloride, bromide, and iodide, the halide anions in the catalyst system generally being of the same type, although different halide anions may also be used.

The amount of the alkali metal salts may range from 0 to 200 mole percent, based on the palladium(II) salt present.

The molar ratio of palladium(II) ions to copper ions is equal to or greater than 0.2.

As a guide, the content of palladium(II) salts should range from 0.1 to 2.0 millimoles and the content of copper salts from 0.1 to 10.0 millimoles, per 100 milliliters of the alcohol. A molar ratio of halide to carboxylate anions from 15:85 to 60:40 will serve as a guide. The amount of halides present in the reaction is preferably limited to 4 moles per mole of palladium.

The present teaching is based, among other things, on the observation that the selectivity (that is to say, the quotient of the quantity of oxalate formed to the quantity of oxalate plus carbonate formed) of the method under discussion increases with decreasing pH values, while the reaction rate has a definite maximum between pH 4.5 and pH 7. In the light of past experience, with pH values under 4 the formation of byproducts (formates, formals, and esters of the carboxylic acids present in the reaction phase) also increases.

There is nothing in the prior art that would have indicated that the reaction is dependent on particular pH values or pH ranges to a degree that has a decided effect on the results.

Thus, according to U.S. Pat. No. 3,994,960, additions of up to about 7 moles of sodium hydroxide solution, for example, per liter of alcoholic reaction phase are contemplated. On the other hand, published German patent application No. DOS 28 14 708 recommends acidic co-catalysts, as mentioned earlier.

The catalyst system to be used in accordance with the invention is distinguished by its simplicity. Working up and regeneration of the system, identification and separation of byproducts, etc., are therefore also simpler and more straightforward than with most prior art processes. When the pH values of the invention are observed, the reaction will remain entirely or predominantly in the pH range which is best for the desired course of the reaction.

The present process is characterized by the reaction of an alcohol with carbon monoxide and oxygen in a liquid phase at elevated pressure and elevated temperature in the presence of a catalyst that is soluble in the liquid phase. Suitable alcohols are primary, secondary and tertiary aliphatic and cycloaliphatic alcohols having from 1 to 10 carbon atoms, preferably alkanols and alcohols of cycloaliphatic hydrocarbons such as methanol, ethanol, n-propanol, isopropanol, n-butanol, n-hexanol, and cyclohexanol, as well as alcohols of araliphatic hydrocarbons, such as benzyl alcohol. The alcohols should be as anhydrous as possible since water in appreciable amounts is known to interfere with the reaction. Inert solvents may be used although they generally are not required. Suitable solvents are aromatics such as benzene or toluene, ethers such as tetrahydrofuran or dioxane, sulfones such as dimethyl sulfone, and esters such as methyl, ethyl, or butyl acetate. However, reaction in pure alcohol or alcohol-oxalic ester mixtures is preferred. The reaction may be carried out at temperatures ranging from 20° C. to 250° C. and at total pressures ranging from 1 to 700 bars so far as selectivity and yield are concerned. The selectivity will increase with increasing pressure and drop with increasing temperature. On the other hand, the reaction rate increases with increasing temperature. In industrial practice, a judicious comprise should therefore be sought since the use of very high pressures is undesirable because of the attendant equipment costs while, on the other hand, a sufficiently high selectivity and yield are desirable. A good comprise is to use temperatures ranging from 70° C. to 200° C., and preferably from 70° C. to 150° C., and carbon monoxide partial pressures of not more than 200 bars, the pressure having at least a numerical value in bars equal to the reaction temperature in degrees Celsius minus 10° C.

The oxygen may be used in pure form or in the form of $O_2/N_2$ mixtures such as air. The $CO/O_2$ ratio should not be less than 4:1, which corresponds to the stoichiometry of the reaction. If it is desired to use nonexplosive gas mixtures, it will be advisable to use an excess of carbon monoxide and to feed in the oxygen as it is consumed. In discontinuous operation, such feed-in may be effected batchwise and in continuous operation it may be effected continuously to maintain a constant oxygen partial pressure.

The reaction time may vary. Times from ½ to 2½ hours are suitable. Mixtures of palladium(II) salts and copper(II) salts which are soluble in the reaction phase, for example $PdCl_2$, $PdBr_2$, $PdI_2$, $Cu(OAc)_2$, $CuCl_2$, $CuBr_2$, or $Pd(OAc)_2$ are suitable as catalysts. To increase the solubility, alkali metal salts such as LiCl, KBr, LiOAc, or potassium pivalate may be added. Only halides and carboxylates should be used and the amount of halide per mole should not be more than four times the amount of palladium per mole. Moreover, it is important to select the composition of the catalyst so that the formal pH value of the solution is between 5 and 8. The following catalyst compositions will be suitable: $PdCl_2/Cu(OAc)_2$, $PdBr/Cu(OAc)_2$, $PdI_2/Cu(OAc)_2$, $K_2PdBr_4/Cu(OAc)_2$, $K_2PdI_4/Cu(OAc)_2$, and $Pd(OAc)_2/CuCl_2/Cu(OAc)_2$. In addition to the acetates, propionates, pivalates, isobutyrates, chloroacetates, and benzoates, other carboxylates may be used. The palladium(II) salts may be used in amounts from 0.1 to 2.0 millimoles and the copper salts in amounts of from 0.1 to 10 millimoles, both per 100 milliliters of the alcohol. To obtain good selectivity, the copper ions should not be used in a large excess. A ratio of Cu(II)/Pd(II) equal to or less than 5 has proved appropriate. As materials for construction of the reactor, nickel-containing high-grade steels or tantalum are suitable. The simplest way of working up the reaction mixture is by fractional distillation in a vacuum.

The products obtained by this process were analyzed by gas chromatography.

The following examples will serve to illustrate the invention.

EXAMPLES

General description of tests

In each case, 100 cc of a solution of the catalysts in the respective alcohol was charged to an 0.3-liter autoclave made of "Hastelloy C 4" (see Ullmanns Enzyklopaedie der technischen Chemie, 3rd ed., vol. 1, p. 940. Urban & Schwarzenberg, 1951) equipped with an electric heating system and a magnetic stirrer. Then, carbon monoxide and air were injected and the charge was heated to the reaction temperature. The pH value of the solutions at the start of the reaction, the carbon monoxide and air pressures used, the reaction time and reaction temperature, as well as the yield and selectivity are given in the Tables which follow.

Measurement of formal pH values

The pH values of the alcoholic solutions (reaction phase) were determined with a glass electrode as in the case of aqueous solutions. The electrode was calibrated as for aqueous systems using standardized buffer solutions. Analysis was also analogous to that commonly used with aqueous systems, the formal pH value being computed by the equation given on page 5. (See K. Schwabe, "Elektrochemische pH-Messungen unter extremen Bedingungen", Verlag Chemie, 1960.)

The pH value decreases in the course of the reaction. In some embodiments, it may drop below pH 5 and even below pH 3. But in the light of past experience, such a reaction segment is not likely to make a positive contribution to the reaction at such a low pH value.

| Example No. | Alcohol | Catalyst system Amount Millimoles | Composition | pH prior to reaction | Initial pressure Bars CO | Air | Reaction time hr. | temperature °C. | Oxalate content of reaction product Wt. % | Oxalate/ carbonate ratio |
|---|---|---|---|---|---|---|---|---|---|---|
| 1 | $CH_3OH$ | 0.5 | $Pd(OAc)_2$ | 7.2 | 70 | 80 | 2.5 | 80 | 10.5 | 86:14 |
|   |   | 1.8 | $CuCl_2$ |   |   |   |   |   |   |   |
|   |   | 3.6 | KOAc |   |   |   |   |   |   |   |
| 2 | $CH_3OH$ | 1.8 | $PdCl_2$ | 6.6 | 70 | 70 | 3 | 80 | 13.4 | 82:18 |
|   |   | 3.6 | LiCl |   |   |   |   |   |   |   |
|   |   | 15.9 | $Cu(OAc)_2$ |   |   |   |   |   |   |   |
| 3 | $C_2H_5OH$ | 0.5 | $PdBr_2$ | 6.8 | 70 | 80 | 3 | 80 | 9.1 | 93:7 |
|   |   | 1.8 | $Cu(OAc)_2$ |   |   |   |   |   |   |   |
| 4 | $i\text{-}C_3H_7OH$ | 0.5 | $PdBr_2$ | 7.6 | 70 | 80 | 5 | 80 | 12.5 | 86:4 |
|   |   | 1.8 | $Cu(OAc)_2$ |   |   |   |   |   |   |   |
| 5 | $n\text{-}C_4H_9OH$ | 0.5 | $PdBr_2$ | 7.2 | 70 | 80 | 3 | 80 | 8.9 | 96:4 |
|   |   | 1.8 | $Cu(OAc)_2$ |   |   |   |   |   |   |   |
| 6 | Cyclo-hexanol | 0.5 | $PdBr_2$ | 7.2 | 70 | 80 | 3 | 80 | 8.6 | 94:6 |
|   |   | 1.8 | $Cu(OAc)_2$ |   |   |   |   |   |   |   |
| 7 | $n\text{-}C_6H_{13}\text{—}OH$ | 0.5 | $PdBr_2$ | 7.2 | 70 | 80 | 3 | 80 | 6.6 | 85:15 |

| Example No. | Alcohol | Catalyst system Amount Millimoles | Composition | pH prior to reaction | Initial pressure Bars CO | Air | Reaction time hr. | temperature °C. | Oxalate content of reaction product Wt. % | Oxalate/ carbonate ratio |
|---|---|---|---|---|---|---|---|---|---|---|
| | | 1.8 | Cu(OAc)$_2$ | | | | | | | |

What is claimed is:

1. A method for making a diester of oxalic acid which comprises oxidatively carbonylating an alcohol having 1 to 10 carbon atoms with carbon monoxide and with oxygen at a pressure from 1 to 700 bars and at a temperature from 20° C. to 250° C. in an initally anhydrous reaction phase comprising said alcohol having dissolved therein a catalyst system consisting essentially of, as cations, ions of palladium(II) and of copper in a molar ratio of at least 0.2, together with alkali metal ions, and, as anions, halide ions and carboxylate ions having 1 to 6 carbon atoms, the amounts of all ions in said catalyst system being such that the solution of the cations and anions in the reaction phase a formal pH value, as determined electrisetrically, between 8 and 5.

2. A method as in claim 1 wherein the carbon monoxide partial pressure, expressed in bars, has a greater numerical value than the value of the reaction temperature, expressed in degrees Celsius, minus 10° C.

3. A method as in claim 1 wherein the reaction temperature is at least 70° C.

4. A method as in claim 3 wherein the reaction temperature is from 70° C. to 200° C.

5. A method as in claim 1 wherein the molar ratio of carbon monoxide to oxygen is at least 4:1.

6. A method as in claim 1 wherein the copper ions are copper(II) ions.

7. A method as in claim 1 wherein the content of palladium(II) salt is from 0.1 to 2.0 millimoles and the content of copper salt is 0.1 to 10 millimoles, per 100 milliliters of alcohol.

8. A method as in claim 1 wherein those catalyst anions which are not halide anions are acetate ions.

9. A method as in claim 1 wherein the ratio of the moles of halide anions present in the reaction phase to the moles of palladium present does not exceeds 4:1.

10. A method as in claim 1 wherein said diester is dimethyl oxalate and is produced with a space-time yield of at least 10 grams/liter hour.

* * * * *